United States Patent
Hansen et al.

(10) Patent No.: US 8,043,256 B2
(45) Date of Patent: Oct. 25, 2011

(54) RAPID EXCHANGE BALLOON CATHETER AND METHOD FOR MAKING SAME

(75) Inventors: Palle M. Hansen, Bjaeverskov (DK); Steen Aggerholm, St. Heddinge (DK)

(73) Assignee: Cook Medical Technologies LLC, Bloomington, IN (US)

( * ) Notice: Subject to any disclaimer, the term of this patent is extended or adjusted under 35 U.S.C. 154(b) by 93 days.

(21) Appl. No.: 12/093,034

(22) PCT Filed: Nov. 16, 2006

(86) PCT No.: PCT/US2006/044495
§ 371 (c)(1),
(2), (4) Date: Sep. 11, 2008

(87) PCT Pub. No.: WO2007/059281
PCT Pub. Date: May 24, 2007

(65) Prior Publication Data
US 2009/0149808 A1    Jun. 11, 2009

(51) Int. Cl.
*A61M 29/00* (2006.01)
(52) U.S. Cl. .................................................. 604/96.01
(58) Field of Classification Search .................. 606/192, 606/194; 604/96.01, 103.04; 623/1.11
See application file for complete search history.

(56) References Cited

U.S. PATENT DOCUMENTS

| | | | | |
|---|---|---|---|---|
| 6,068,623 | A  * | 5/2000 | Zadno-Azizi et al. | 604/530 |
| 6,575,958 | B1 * | 6/2003 | Happ et al. | 604/525 |
| 6,746,423 | B1   | 6/2004 | Wantink | |
| 2001/0037085 | A1 | 11/2001 | Keith et al. | |
| 2003/0125709 | A1 * | 7/2003 | Eidenschink | 604/524 |
| 2004/0006360 | A1 | 1/2004 | Garakani | |

FOREIGN PATENT DOCUMENTS

| | | |
|---|---|---|
| WO | WO 95/24236 A1 | 9/1995 |
| WO | WO 03/041783 A1 | 5/2003 |

OTHER PUBLICATIONS

International Search Report completed Mar. 28, 2007 for International Application No. PCT/US2006/044495.

* cited by examiner

*Primary Examiner* — Christopher D Koharski
(74) *Attorney, Agent, or Firm* — Brinks Hofer Gilson & Lione

(57) ABSTRACT

A rapid exchange balloon catheter having a proximal end and a distal end, said catheter comprising: a tubular metal shaft body extending from the proximal end along a majority of the total length and having an inflation lumen arranged therein, a plastics distal end portion bonded to the metal body in extension thereof, said distal end portion being provided with an inflation lumen in communication with a balloon, and a guide wire lumen, said guide wire lumen extending from a proximal side port to a distal end opening. To reduce the resistance to kinking, the metal body comprises a transitional region having reduced stiffness at the position of bonding to the plastics distal end portion compared to a more proximal position along the metal body.

13 Claims, 2 Drawing Sheets

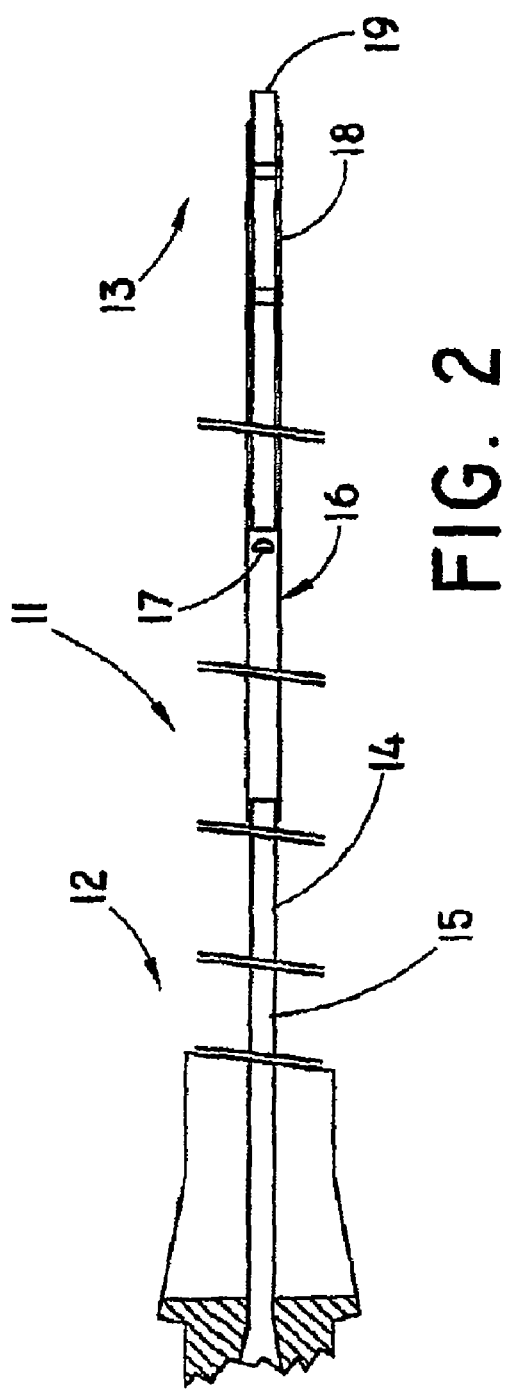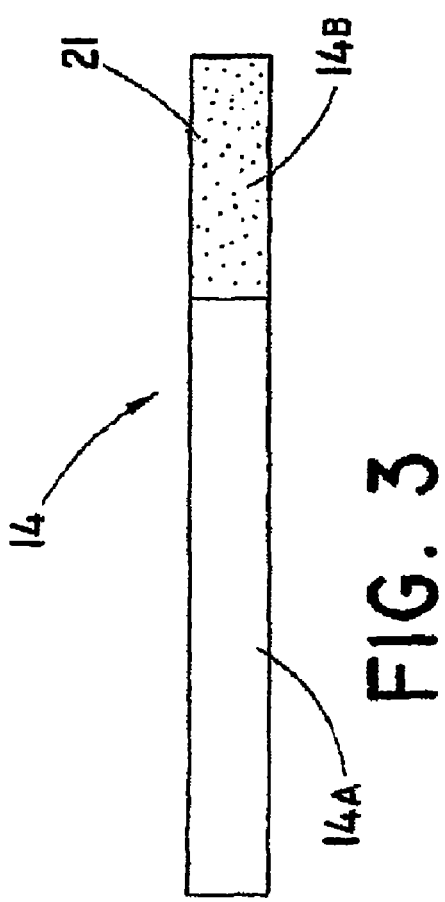

RAPID EXCHANGE BALLOON CATHETER AND METHOD FOR MAKING SAME

This application is a continuation of International Application No. PCT/US2006/044495, filed Nov. 16, 2006, which claims the benefit of U.S. Provisional Application Ser. No. 60/737,124, filed Nov. 16, 2005. These references are incorporated herein in their entirety.

TECHNICAL FIELD

The present invention relates to a rapid exchange balloon catheter.

BACKGROUND OF THE INVENTION

Catheters have found widespread use in medical procedures, such as percutaneous transluminal coronary angioplasty (PTCA) or for delivery of stents. Most catheters are guided to the application site by sliding the catheter along a guide wire, which has been carefully advanced and arranged within the patient. During advancement of the catheter along the guide wire, it is important to keep the guide wire steady. Ordinary catheters are guided to the application site in a patient by sliding the catheter along a guide wire extending all the way through a lumen of the catheter from the proximal end to the distal end thereof. To enable the physician to hold or manipulate the guide wire during advancement of the catheter along the guide wire, it is necessary to have an excess length of guide wire. The guide wire must hence have a length of about twice the length of the catheter, e.g. 3 m in total, which greatly impedes the procedure. An important sub-category of catheters are catheters of the well-known so-called rapid exchange type, which greatly facilitate operation, especially exchange of catheters if it is found during a procedure that a different kind or size of catheter is needed for the specific purpose. In the rapid exchange catheter, the guide wire only passes through a minor part of the catheter at the distal end thereof, whereas along a majority of the catheter, the guide wire runs in parallel with the catheter. Hence it is not necessary to have an excess length of guide wire. However the rapid exchange catheter provides some challenges, especially with regard to resistance to kinking of the catheter.

An important feature of catheters is the transmission of force, the so-called push force, from the proximal end to the distal end of the catheter. This transmission significantly affects the physician's ability to direct the distal end of the catheter into a body lumen of a patient by manipulating the proximal end thereof. Another important feature of catheters is the flexibility of the distal end to bend and conform to the body lumen wall without causing any injury to the lumen wall. Hence catheters, especially of the rapid exchange type, are commonly manufactured of a metal proximal shaft portion of relatively stiffness, and a relatively flexible plastics distal portion bonded to the metal shaft portion. An abrupt change of properties between the shaft portion and the distal portion however increases the risk of twist and kinking. Hence there is a need to provide a good transition between the relatively stiff proximal section to the relatively more flexible distal section to provide a sufficient resistance to twist and kinking while maintaining flexibility and ability to bend.

U.S. Pat. No. 6,746,423 discloses a catheter with a reinforcing member at a rapid exchange junction. Although this construction has some effect on the kink resistance, it is somewhat difficult to manufacture and hence expensive. This is due to the fact that the construction introduces a separate element, namely a reinforcing member, which must be securely bonded to the catheter. The reinforcing member must be stocked and handled inevitably raising the cost, and further there is an increased risk of leakage from the catheter due to the extra joints, thereby raising the costs to skilled personnel and quality check.

It is hence an object of the invention to provide an alternative catheter with reduced risk of kinking.

SUMMARY OF THE INVENTION

The present invention relates to a rapid exchange balloon catheter having a proximal end and a distal end, said catheter comprising: a tubular metal shaft body extending from the proximal end along a majority of the total length and having an inflation lumen arranged therein, a plastics distal end portion bonded to the metal body in extension thereof, said distal end portion being provided with an inflation lumen in communication with a balloon, and a guide wire lumen, said guide wire lumen extending from a proximal side port to a distal end opening.

The metal body comprises a transitional region having reduced stiffness at the position of bonding to the plastics distal end portion compared to a more proximal position along the metal body. By providing a reduced stiffness transitional region in the metal body, there is avoided an abrupt junction from the relatively stiff metal body to the relatively flexible plastics distal end portion. Through the provision of an integral transitional region with reduced stiffness in the metal body, a separate reinforcing member is obviated, and the disadvantages associated therewith avoided.

According to an embodiment the stiffness is defined as bending stiffness, where said bending stiffness of the metal body at a proximal position is at least twice as high as the bending stiffness of the metal body at the distal end of the transitional region. Some effect may be provided with a transitional region having a bending stiffness which does not meet this requirement, but the effect is found to be less than optimum.

The effect is more pronounced when the bending stiffness of the metal body at a proximal position is at least four times, preferably at least eight times as high as the bending stiffness of the metal body at the distal end of the transitional region.

A catheter having very favourable properties in relation to kink resistance may be provided by a catheter wherein the bending stiffness of the metal body at a proximal position is at least twenty times as high as the bending stiffness of the metal body at the distal end of the transitional region. Hereby a very smooth transition between the relatively stiff metal body and the relatively flexible plastics portion is provided, and hence the risk of kinking is very low.

The catheter may be made from any suitable metal material, such as stainless steel, which is a well-known and relatively low cost material. According to an embodiment, however, the metal body is at least partly made of a shape memory nickel-titanium alloy. Such nickel-titanium (Nitinol) alloys are superelastic and are found to provide catheters having increased pushability and torquability in the narrow bends and curvature of the vascular system of a patient.

According to an embodiment the transitional region has a length of 1 to 50 mm, preferably at least 5 mm and less than 25 mm, and preferably about 10 mm. As is evident to the skilled person, the chosen length of the transitional region is a compromise between contradictory requirements. A length of less than 1 mm would normally not be sufficient to provide a satisfactory transitional region as such a short length will entail a relatively abrupt change of properties. Length in excess of 50 mm would normally not have any positive effect on the kink resistance, and may increase the cost of the catheter. A length of about 10 mm is found to provide a favourable compromise, but lengths of between 5 mm and 25 mm is expected to provide good results, depending on the size of the catheter and the materials used.

The reduced stiffness of the transitional region may be accomplished in any suitable way, and according to an embodiment the transitional region comprises weakenings, such as cut-outs, reduced wall thickness or the like. Such machining is relatively cheap and can be performed with e.g. laser cutting. A gradual transition can be achieved by careful choice of size and spacing of the weakenings.

According to an alternative or supplementary embodiment the transitional region has been subject to heat treatment at temperatures of 300-600° C. for a period of 10 s to 24 h, whereby the physical properties of the nitinol alloy is permanently altered, and inter alia the stiffness is reduced. Different alloys may respond differently to heat treatment, and the choice of temperature and processing period is a compromise between speed of manufacture, cost of the process and the effect achieved. The skilled person would recognise that the process period should be chosen as short as possible, but a period of less than 10 s will normally not be enough to change the physical properties of the alloy, even for diminutive objects, such as the end of a small diameter catheter. On the other hand processing periods of more than 24 hours increases the processing cost significantly, and should be avoided, and further longer processing times will normally not have any substantial effect on the physical properties of relatively small objects like catheters.

Another aspect of the invention relates to a method for manufacturing a rapid exchange balloon catheter comprising the steps of: providing a tubular metal shaft body with an inflation lumen arranged therein, providing a plastics distal end portion, said distal end portion being provided with an inflation lumen in communication with a balloon, and a guide wire lumen, said guide wire lumen extending from a side port to a distal end opening, subjecting an end of the tubular metal shaft body to a processing step adapted to locally reduce the stiffness of an end region of the tubular metal shaft body to provide a transitional region, and bonding the plastics distal end portion onto said transitional region. Hereby a relatively low cost and consistent method for making a rapid exchange catheter is provided, whereby a high quality catheter with improved kink resistance can be manufactured.

According to an embodiment, the tubular metal shaft body is made of a superelastic alloy, and wherein the processing step involves heat treating the transitional region at temperatures of 300-600° C. for a period of 10 s to 24 h. The heat treatment may be accomplished by dipping the transitional region into a heated salt bath.

BRIEF DESCRIPTION OF THE DRAWING

In the following the invention will be described in more detail, by way of example only, and with reference to the drawing, in which FIG. 2 is a side view of a catheter according to the invention, and FIG. 3 is an enlarged schematic view of FIG. 2 of a shaft portion with transitional region.

DETAILED DESCRIPTION

Figure 1:
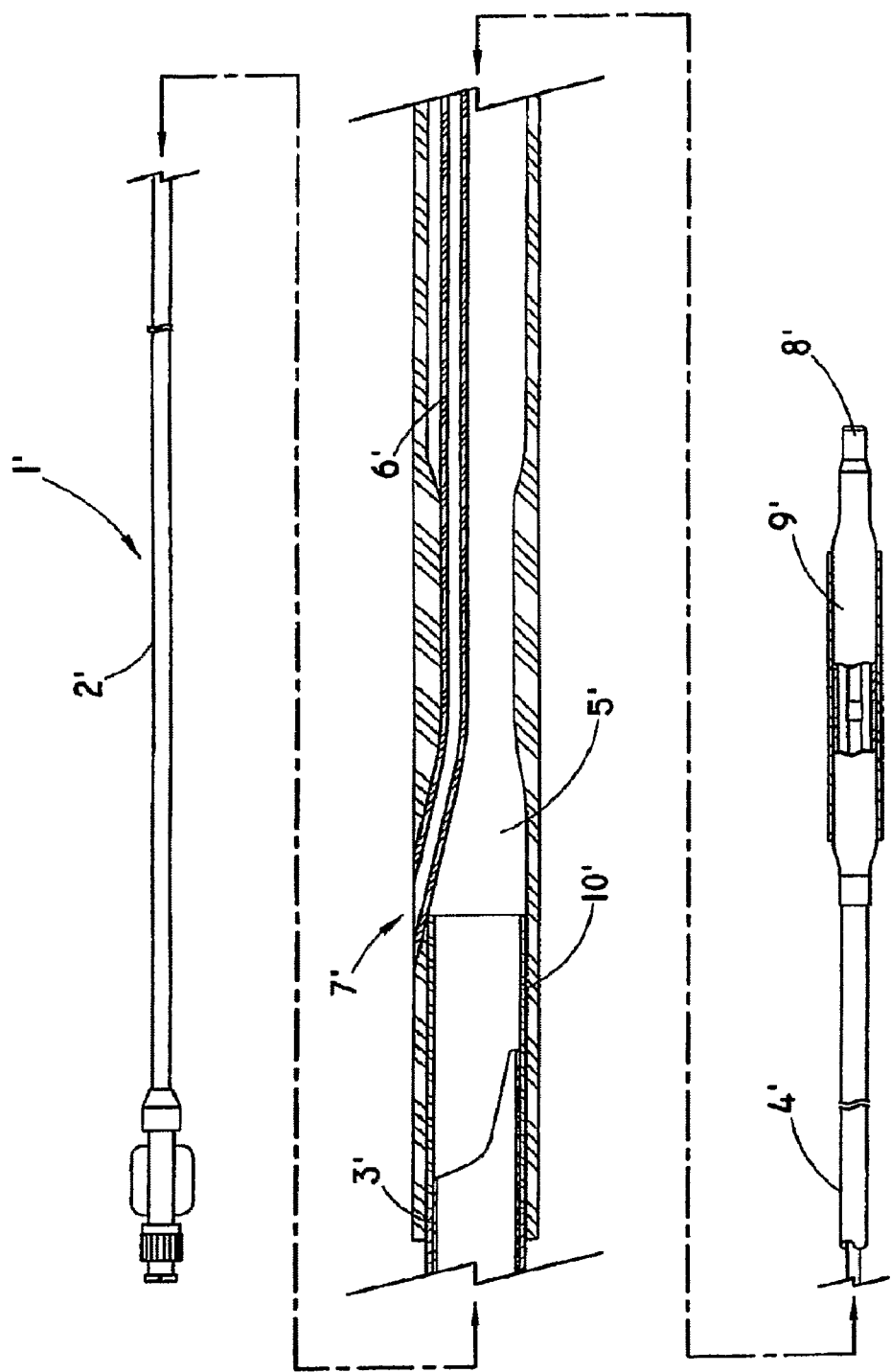
FIG. 1 is a side view, partly in section, of a prior art catheter.

A prior art rapid exchange catheter according to U.S. Pat. No. 6,746,423 as discussed above is seen in FIG. 1. This prior art catheter 1' comprises a tubular metal shaft body 2' extending from the proximal end along a majority of the total length and having an inflation lumen 3' arranged therein. The catheter 1' further comprises a plastics distal end portion 41 bonded to the metal body in extension thereof. The distal end portion 4' is provided with an inflation lumen 5' and a guide wire lumen 6', said guide wire lumen 6' extending from a proximal side port 7' to a distal end opening 8'. The catheter 1' further comprises a balloon 9' arranged at the distal end of the catheter. This prior art catheter 1' further incorporates a reinforcing member 10' in form of a tube bridging the region of junction between the metal body 2' and the plastics distal end portion 4'.

In FIG. 2 is shown a catheter according to the invention. This figure is somewhat distorted for illustration purposes, as the total length of the catheter is about 140 cm. The catheter 11 has a proximal end 12 and a distal end 13. The catheter 11 comprises tubular metal shaft body 14 made of a nitinol alloy. An inflation lumen 15 is extending in the full length of the metal shaft body 14. A plastics distal end portion 16 is attached to the end of the tubular metal shaft body 14 by bonding. The plastics distal end portion 16 comprises a side port 17 for a guide wire (not shown) at a proximal side of an inflatable balloon 18, so the guide wire may extend through the most distal part of the catheter to the distal end opening 19.

FIG. 3 is a schematic illustration of a part of the tubular metal shaft body 14 of the catheter in FIG. 2. As illustrated the tubular metal shaft body 14 comprises a main region 14a and a transitional region 14b, and the main region 14a and the transitional region 14b are integral. However the bending stiffness of the transitional region 14b is substantially lower than the bending stiffness of the main region 14a. In the embodiment the tubular metal shaft body 14 is made of a nitinol alloy. The bending stiffness may be defined as the resistance to bending when a beam is subjected to a load in transverse direction. As an example one tubular metal shaft body having high bending stiffness may deflect by e.g. 5 mm when a 20 N force is applied at the end of the shaft body in a direction at right angles to the longitudinal direction of the shaft, whereas a similar tubular metal shaft body relatively having low bending stiffness may deflect 20 mm in response to the same load. According to an embodiment, the transitional region comprises weakenings 21, such as cut-outs, reduced wall thickness or the like.

A prototype of the catheter according to the invention used Nitinol SE508 tubing available from NDC (Nitinol Devices & Components). The composition of this particular nickel-titanium alloy (in weight percent) is as follows: Nickel (nominal): 55.8%, Titanium: balance, Oxygen (max): 0.05%, Carbon (max): 0.02%. The properties of nitinol alloys are dependent on processing history and ambient temperature, and for example Modulus of Elasticity of this alloy is given as an interval of $41\text{-}75 \times 10^3$ MPa. The delivered tubes had an outer diameter of 0.25 mm and an inner diameter of approx 0.20 mm. The tubes delivered from NDC had an overall transition temperature below 18° C. The tubes were cut to have a length of 10.00 cm and divided in first part (5.0 cm) and a second part (5.0 cm).

Nickel-titanium alloys, such as nitinol, are known to possess special properties, e.g. shape memory and superelastic properties. Nitinol is capable of reversible thermoelastic transformation due to phase transition.

The second part was subjected to the following thermal treatment (performed by ADMEDES Schuessler, Germany): the second part was placed in a salt bath heated to 540-550° C. for approx 20 hours, while the first part was kept cool as close to room temperature as possible. After the thermal treatment, the second part of the nitinol tubes had a transition temperature in the range of about 28-32° C. Thus, above 32° C. the second part of the tubes was in an austenitic phase with a relatively high bending stiffness. Below 28° C. the second part of the tubes was in a Martensitic phase with a significantly lower bending stiffness. The first part of the tubes maintained a transition temperature below 18° C. and appeared rather stiff.

Shorter or longer periods may be used as may higher or lower temperatures, depending on the material being heat treated and the desired properties of the material. With the above material, the range of parameters should be approximately 520-600° C. and 30 minutes to 24 hours.

By locally heat treating regions of the metal body, it is possible to produce a metal body with spatial variations in physical properties, such as elasticity and stiffness of the metal body. Depending on the extent of the heat treatment, the metal material may simply have a reduced stiffness in the locally treated region or the superelasticity of the locally treated portion may be destroyed, so this region is plastically deformable.

By the local heat treatment of the superelastic alloy, the Modulus of Elasticity (i.e. the stress-strain behaviour of the material or stiffness) of different regions can be different due to different phases of the alloy, e.g. Austenitic phase or Martensitic phase. Hence in one region the alloy may exhibit superelastic properties (highly flexible), whereas in another region the alloy may exhibit plastic properties. The Modulus of Elasticity (or stiffness) of the two regions would be different and hence the stress-strain behaviour would be different.

According to an embodiment the tubular metal shaft body 14 made of nitinol is subjected to a localized heat treatment to provide a transitional region 14b having reduced stiffness. This localized heat treatment may be accomplished by any suitable method, such as dipping into a hot salt bath as mentioned above. Alternative methods include electrical resistance heating, laser heating, using a jet of hot inert gas, or using an induction coil to heat the desired portion to provide a transitional region.

Suitable materials for the plastics distal end portion include for example various synthetic polymer materials, polyimid, polyamid etc., and other materials as will be evident to the skilled person.

The inner diameter of the proximal end of the plastics distal end portion could be chosen to be slightly larger than the outer diameter of the tubular metal body shaft distal end, so the plastics distal end portion can be slid onto the tubular metal body shaft and bonded thereto. Bonding may be accomplished by a suitable type of glue or by thermal bonding of the plastics distal end portion to the metal body, such as by using a laser.

The invention claimed is:

1. A rapid exchange balloon catheter having a proximal end and a distal end, said catheter comprising:
   a tubular metal shaft body extending from the proximal end along a majority of the total length and having an inflation lumen arranged therein, the metal body comprising an integral transitional region at a distal end region of the metal body,
   a plastics distal end portion comprising a proximal portion bonded onto the transitional region of the metal body and the plastics distal end portion comprising a distal portion extending distal to the metal body,
   said plastics distal end portion being provided with an inflation lumen in communication with a balloon, and a guide wire lumen, said guide wire lumen extending from a proximal side port of said plastics distal end portion to a distal end opening,
   wherein the transitional region has reduced stiffness at a region of bonding of the proximal portion of the plastics distal end portion onto the transitional region compared to a more proximal position along the metal body, the stiffness is defined as bending stiffness and the transitional region has been subjected to heat treatment to reduce the bending stiffness of the transitional region compared to the more proximal position.

2. A catheter according to claim 1, wherein said bending stiffness of the metal body at a proximal position is at least twice as high as the bending stiffness of the metal body at the distal end of the transitional region.

3. A catheter according to claim 1, wherein the bending stiffness of the metal body at a proximal position is at least four times as high as the bending stiffness of the metal body at the distal end of the transitional region.

4. A catheter according to claim 1, wherein the bending stiffness of the metal body at a proximal position is at least 8 times as high as the bending stiffness of the metal body at the distal end of the transitional region.

5. A catheter according to according to claim 1, wherein the bending stiffness of the metal body at a proximal position is at least twenty times as high as the bending stiffness of the metal body at the distal end of the transitional region.

6. A catheter according to claim 1, wherein the metal body is at least partly made of a shape memory metal or a superelastic nickel-titanium alloy.

7. A catheter according to claim 1, wherein the transitional region has a length of 1 to 50 mm.

8. A catheter according to claim 1, wherein the transitional region has a length of at least 5 mm and less than 25 mm.

9. A catheter according to claim 1, wherein the transitional region has a length of about 10 mm.

10. A catheter according to claim 1, wherein the transitional region comprises weakenings.

11. A catheter according to claim 1, wherein the shape and dimension of the tubular metal shaft body is substantially unchanging in the transitional region.

12. A catheter according to claim 6, wherein the transitional region has been subject to heat treatment at temperatures of 300-600° C. for a period of 10 s to 24 h.

13. The catheter according to claim 10, wherein the weakenings are selected from the group consisting of cut-outs and reduced wall thickness.

* * * * *

UNITED STATES PATENT AND TRADEMARK OFFICE
CERTIFICATE OF CORRECTION

| | | |
|---|---|---|
| PATENT NO. | : 8,043,256 B2 | Page 1 of 1 |
| APPLICATION NO. | : 12/093034 | |
| DATED | : October 25, 2011 | |
| INVENTOR(S) | : Palle M. Hansen et al. | |

It is certified that error appears in the above-identified patent and that said Letters Patent is hereby corrected as shown below:

On the Title Page

After Item (65) insert a new item as follows.

--Related U.S. Application Data
This application is a continuation of International Application
No. PCT/US2006/044495, filed November 16, 2006, which claims
the benefit of U.S. Provisional Application No. 60/737,124, filed
November 16, 2005.--

In column 6, claim 5, line 33, after "A catheter" delete "according to" (second occurrence).

In column 6, claim 12, line 53, replace "300-600° C." with --300-600°C.--.

Signed and Sealed this

Nineteenth Day of June, 2012

David J. Kappos
*Director of the United States Patent and Trademark Office*